US012624852B2

(12) United States Patent
Lee et al.

(10) Patent No.: US 12,624,852 B2
(45) Date of Patent: May 12, 2026

(54) AIR CONDITIONING SYSTEM AND METHOD FOR DISINFECTION OF PUBLIC FACILITIES

(71) Applicant: KOREA INSTITUTE OF MATERIALS SCIENCE, Changwon-si (KR)

(72) Inventors: Seung-hoon Lee, Changwon-si (KR); Do-geun Kim, Seoul (KR); Chang-su Kim, Changwon-si (KR); Joo-young Park, Changwon-si (KR); Sung-hoon Jung, Changwon-si (KR); Joon-hwan Choi, Changwon-si (KR); Eun-yeon Byeon, Changwon-si (KR); Jong-man Lee, Changwon-si (KR); Jang-hoon Ha, Changwon-si (KR); Sang-jin Kim, Changwon-si (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 621 days.

(21) Appl. No.: 18/092,363

(22) Filed: Jan. 2, 2023

(65) Prior Publication Data

US 2023/0151986 A1 May 18, 2023

Related U.S. Application Data

(63) Continuation of application No. PCT/KR2022/001392, filed on Jan. 26, 2022.

(30) Foreign Application Priority Data

Apr. 21, 2021 (KR) ........................ 10-2021-0051813

(51) Int. Cl.
*A61L 9/22* (2006.01)
*F24F 7/08* (2006.01)
(Continued)

(52) U.S. Cl.
CPC ..................................... *F24F 8/26* (2021.01); *A61L 9/22* (2013.01); *F24F 7/08* (2013.01); *F24F 8/167* (2021.01);
(Continued)

(58) Field of Classification Search
CPC ........................................................ A61L 9/22
See application file for complete search history.

(56) References Cited

U.S. PATENT DOCUMENTS

| | | | |
|---|---|---|---|
| 2006/0087243 A1* | 4/2006 | Zhan .................... | H05H 1/2406 315/111.21 |
| 2006/0150818 A1* | 7/2006 | Okamoto ................. | F24F 8/30 96/223 |

(Continued)

FOREIGN PATENT DOCUMENTS

| | | |
|---|---|---|
| JP | 2002361028 | 12/2002 |
| JP | 2011-158247 | 8/2011 |

(Continued)

OTHER PUBLICATIONS

KIPO, Office Action of the corresponding Korean Patent Application No. 10-2021-0051813,dated Oct. 21, 2022, total 8 pages.

*Primary Examiner* — Kevin Joyner
(74) *Attorney, Agent, or Firm* — LEX IP MEISTER, PLLC

(57) ABSTRACT

The present disclosure relates to an air conditioning system and method for disinfection of a public facility. More specifically, the present disclosure relates to an air conditioning system and method for disinfection of a public facility capable of sterilizing or inactivating bio-aerosols existing in interior space by using the air conditioning equipment installed in the public facility structures.

19 Claims, 9 Drawing Sheets

(51) Int. Cl.

| | | |
|---|---|---|
| *F24F 8/167* | (2021.01) | |
| *F24F 8/192* | (2021.01) | |
| *F24F 8/26* | (2021.01) | |
| *F24F 8/98* | (2021.01) | |

(52) U.S. Cl.

CPC ................ *F24F 8/192* (2021.01); *F24F 8/98* (2021.01); *A61L 2209/14* (2013.01); *A61L 2209/16* (2013.01)

(56) References Cited

U.S. PATENT DOCUMENTS

| | | | |
|---|---|---|---|
| 2014/0205495 A1* | 7/2014 | Ota | A61L 9/22 422/4 |
| 2014/0326428 A1* | 11/2014 | Meirav | B01D 53/0446 165/59 |
| 2017/0274113 A1 | 9/2017 | Takasahara et al. | |

FOREIGN PATENT DOCUMENTS

| | | |
|---|---|---|
| JP | 5475319 | 4/2014 |
| KR | 20-0408280 | 2/2006 |
| KR | 10-1320703 | 10/2013 |
| KR | 10-1577567 | 12/2015 |
| KR | 10-2059380 | 12/2019 |
| KR | 10-2198329 | 1/2021 |

* cited by examiner

FIG.10

| DFD gaseous ozone generation condition | | |
|---|---|---|
| Diff. Pressure | 27 Pa | Humidity | 66 % |
| Total Power (from Wall power supply) | 14.6 W | Speed of flowing fluid | 1 m/s |
| Temperature | 22 °C | Ozone concentration | 0.55 ± 0.02 ppm(volume) |

| DFD + ozone concentration of catalyst-integrated parts | | | | | |
|---|---|---|---|---|---|
| Emitted ozone concentration [ppb(volume)] | | | | | |
| Time [s] | 0 | 100 | 200 | 300 | 400 | 500 |
| Emitted gas temperature 27°C | 67.9 | 67.7 | 68.4 | 71.2 | 71.9 | 72.8 |

AIR CONDITIONING SYSTEM AND METHOD FOR DISINFECTION OF PUBLIC FACILITIES

TECHNICAL FIELD

This disclosure relates to an air conditioning system and method for disinfection of a public facility. More specifically, this disclosure relates to an air conditioning system and method for disinfection of a public facility using an air conditioner of the public facility capable of sterilizing or deactivating indoor bio-aerosols.

BACKGROUND

There exist a lot of bio-aerosols or pathogens which comprehensively refer to microorganisms such as viruses, bacteria or fungi that are harmful to human bodies in public facilities, such as hospitals, schools, public transportations, airports, etc. Their entrance to the body through respiratory system or contact with body may possibly cause diseases. Some are highly contagious so that a lot of pathogenic infections or casualties may be caused within a short period.

For example, as seen in the cases of Middle East Respiratory Syndrome (MERS) and Coronavirus disease-2019 (COVID-19), there is a problem in that the occurrence of secondary infections may rapidly increase due to the lack of management skills for pathogens in the indoor air of public facilities.

In order to solve the problem, it is necessary to periodically manage indoor air quality to remove pathogens and, in case of indoor contamination by pathogens, immediately control the area to take preventive measures against spread of pathogens. However, without specifically implemented system as above, there is a problem in that the preventive measures against the spread of infectious diseases may be delayed due to insufficient response to infectious diseases caused by bio-aerosols.

Furthermore, in case of contamination of a duct inside an air conditioning system of a public facility, recirculation of indoor air may accelerate spread of infectious diseases and generate undesirable odor.

In addition to the problems, according to increasing social demand for an indoor environment safe from pathogens, need for an air conditioning system for effective removal and prevention of spread of bio-aerosol or pathogens in the air is increasing.

As a background art of this disclosure, a device for forming isolation chamber and method for cleaning and fumigating isolation chamber is disclosed in Japanese Patent Registration No. 5475319.

DISCLOSURE

Technical Problem

An object of this disclosure is to provide an air conditioning system and method for disinfection of a public facility capable of collecting, sterilizing and inactivating indoor bio-aerosols using air conditioning equipment of public facilities.

Another object of this disclosure is to provide an air conditioning system and method for disinfection of a public facility with excellent bio-aerosol collection and sterilization performance.

Another object of this disclosure is to provide an air conditioning system and method for disinfection of a public facility with a catalyst unit capable of removing reactive oxygen/nitrogen species such as ozone generated from contaminants or plasma of gas in the air.

Another object of this disclosure is to provide an air conditioning system and method for disinfection of a public facility to effectively take preventive measures against bio-aerosols by optimizing configurations of a plasma filter unit and a catalyst unit according to characteristics of spaces in the public facility.

Another object of this disclosure is to provide an air conditioning system and method for disinfection of a public facility capable of effectively control bio-aerosols by optimized disinfection method according to characteristics of spaces in the public facility.

Another object of this disclosure is to provide an air conditioning system and method for disinfection of a public facility capable of sterilizing and removing undesirable odor from ducts of the air conditioning system of the public facility.

Another object of this disclosure is to provide an air conditioning system and method for disinfection of a public facility to evacuate humans and intensively take indoor preventive measures in case of heavy contamination with pathogens.

Other objects and advantages of this disclosure will become more apparent from the following detailed description, claims and drawings of this disclosure.

Technical Solution

In one aspect, an air conditioning system for disinfection of a public facility comprising: an air conditioning equipment installed in a public facility structure; at least one air supply vent through which air is introduced from the air conditioning equipment to interior space of the public facility; at least one air inlet through which air is exhausted from the interior space of the public facility to the air conditioning equipment; a plasma filter unit installed in at least one of the air supply vent and the air inlet to collect particulate contaminants in air and sterilize or inactivate bio-aerosols with plasma; and a catalyst unit installed in at least one of the air supply vent and the air inlet to remove gaseous contaminants and ozone in air; wherein the air supply vent and the air inlet are installed in each of at least one separate room of the public facility and the plasma filter unit installed in at least one of the air supply vent and air inlet is periodically or continuously operated to periodically or continuously sterilize or inactivate bio-aerosols collected in the plasma filter unit, is provided.

In one embodiment, the plasma filter unit and the catalyst unit in the air conditioning system for disinfection of a public facility may be installed together in the air supply vent or in the air inlet.

In one embodiment of the air conditioning system for disinfection of a public facility, the catalyst unit installed to remove ozone generated from the plasma filter unit may prevent ozone from flowing into interior space or an air conditioning duct.

In one embodiment of an air conditioning system for disinfection of a public facility, operation period of the plasma filter unit in a general disinfection mode may be maintained at less than or equal to 50% of the entire operation period of the air conditioning system for disinfection.

In one embodiment of the air conditioning system for disinfection of a public facility, operation period of the plasma filter unit in an intensive disinfection mode may be maintained at more than 50% to less than or equal to 100% of the entire operation period of the air conditioning system for disinfection.

In one embodiment of the air conditioning system for disinfection of a public facility, the wind speed during the operation of the plasma filter unit may be less than or equal to 2 m/s and concentration of ozone generated from the plasma filter unit may be 0.5 to 100 ppm (volume).

In another aspect, an air conditioning system for disinfection of a public facility, comprising: an air conditioning equipment installed in a public facility structure; at least one air supply vent through which air is introduced from the air conditioning equipment to interior space of the public facility; at least one air inlet through which air is exhausted from the interior space of the public facility to the air conditioning equipment; and a plasma filter unit installed in at least one of the air supply vent and the air inlet to collect particulate contaminants in gas and sterilize or inactivate bio-aerosols with plasma, wherein the air supply vent and the air inlet are installed in each of at least one separate room of the public facility and, the plasma filter unit installed in at least one of the air supply vent and air inlet is periodically or continuously operated to sterilize or inactivate bio-aerosols collected in the plasma filter unit, is provided.

In one embodiment of the air conditioning system for disinfection of a public facility, the plasma filter unit may be installed in the air inlet and the catalyst unit removing gaseous contaminant and ozone in the air may be installed in the air supply vent to prevent remaining ozone from flowing into the interior space.

In one embodiment of the air conditioning system for disinfection of a public facility, the plasma filter unit may be installed in the air inlet to remove bio-aerosols before bio-aerosols generated from at least one separate room contaminates inside the air conditioning equipment of the structure.

In one embodiment of the air conditioning system for disinfection of a public facility, the plasma filter unit may be installed in the air supply vent and when at least one separate room is emptied, operation period of the plasma filter unit may be maintained at more than 50% to less than or equal to 100% of the entire operation period of the air conditioning system as an intensive disinfection mode and generated ozone may pass the air conditioning equipment through air inlet to be emitted to outside of the structure.

In one embodiment of the air conditioning system for disinfection of a public facility, during operation in the intensive disinfection mode, ozone concentration in the separate room or the air conditioning equipment may be maintained at 0.5 to 100 ppm (volume).

In one embodiment of the air conditioning system for disinfection of a public facility, operation period of the plasma filter unit may be individually controlled for each of at least one separate room.

In one embodiment of the air conditioning system for disinfection of a public facility, the plasma filter unit may comprise a plasma generator and a filter.

In one embodiment of the air conditioning system for disinfection of a public facility, the plasma generator may comprise a porous ceramic dielectric and the filter may be at least one group of porous ceramic filters and polymer filters.

In one embodiment of the air conditioning system for disinfection of a public facility, the porous ceramic may be a bead or reticulated porous ceramic.

In one embodiment of the air conditioning system for disinfection of a public facility, the catalyst unit may comprise at least one group of activated carbons and manganese oxide groups.

In another aspect, as a disinfection method of using the air conditioning system for disinfection of a public facility of this disclosure, a general disinfection method of a public facility comprising; i) periodically sterilizing or inactivating bio-aerosols collected in the plasma filter unit for certain period by periodic operation of the plasma filter unit installed in at least one of the air supply vent and the air inlet of at least one separate room; and ii) removing ozone generated from the plasma filter unit in the catalyst unit, is provided.

In one embodiment, a general disinfection method of a public facility may comprise: in step i), collecting particulate matters and sterilizing or inactivating bio-aerosols with ozone in the plasma filter unit by the plasma filter unit and the catalyst unit installed together in the air supply vent or in the air inlet of at least one separate room; and, in step ii), removing ozone generated from the plasma filter unit before flowing into interior space or an air conditioning duct, wherein operation period of the plasma filter unit is maintained at less than or equal to 50% of the entire operation period of the air conditioning system.

In another aspect of disinfection method using the air conditioning system for disinfection of a public facility of this disclosure, an intensive disinfection method, comprising: i) continuously sterilizing or inactivating bio-aerosols collected in the plasma filter unit by continuous operation of plasma filter unit installed in at least one of the air supply vent and air inlet of at least one separate room; and ii) operating in an intensive disinfection mode by maintaining operation period of the plasma filter unit at more than 50% to less than or equal to 100% of the entire operation period and maintaining ozone concentration in the separate room or the air conditioning equipment at 0.5 to 100 ppm (volume), is provided.

In one embodiment, an intensive method for disinfection of a public facility may comprise: in step i), collecting particulate matters in the plasma filter unit installed in the air inlet of at least one separate room and sterilizing or inactivating bio-aerosols with ozone; and removing ozone in the catalyst unit installed in the air supply vent of at least one separate room to prevent ozone from flowing into at least one separate room.

In one embodiment, an intensive disinfection method for disinfection of a public facility may comprise; in step i), when at least one separate room is emptied, disinfecting at least one separate room by generating ozone from the plasma filter unit installed in the air supply vent of at least one separate room; and in completion of the disinfection, emitting remaining ozone in at least one separate room through the air inlet of at least one separate room by passing the air conditioning equipment to outside of the structure.

Advantageous Effects

In one embodiment, an air conditioning system for disinfection of a public facility may be provided with capability of collection, sterilization and inactivation of indoor bio-aerosols by using a filter and a plasma device easily adaptable for an air conditioning equipment of a public facility.

In one embodiment, an air conditioning system for disinfection of a public facility may be provided with a plasma filter unit with high performance in collection and sterilization of bio-aerosols installed in an air supply vent and/or an air inlet.

In one embodiment, a catalyst unit capable of removing oxygen nitrogen active species, such as ozone, generated from gaseous contaminants or plasma in the air may be provided in air supply vent and/or air inlet an air conditioning system for disinfection of a public facility.

In one embodiment, coated layer of a porous ceramic dielectric applied with various sterilizing materials to efficiently remove bio-aerosols, such as specific pathogens, may be provided in an air conditioning system for disinfection of a public facility.

In one embodiment, installation configuration of a plasma filter unit and a catalyst unit optimized to efficiently take preventive measures against bio-aerosols according to characteristics of space may be provided in an air conditioning system for disinfection of a public facility.

In one embodiment, an air conditioning system for disinfection of a public facility, comprising an operation mode to sterilize filter in an air conditioning supply vent by generation of high concentration ozone under a low wind speed condition for a part of the entire operation period and emit the ozone outside, may be provided.

In one embodiment, an air conditioning system for disinfection of a public facility, comprising an operation mode to sterilize the filter installed in the air conditioning inlet by generation of low concentration ozone during the entire operation period and supply air to the interior space by removing remaining ozone, may be provided.

In one embodiment, an air conditioning system for disinfection of a public facility may be provided to efficiently sterilize and remove undesirable odor of a duct of an air conditioning equipment.

In one embodiment, in case of severe indoor contamination by pathogens, an air conditioning system capable of intensive disinfection of a public facility may be provided comprising an operation mode to evacuate humans and maintain high concentration by supplying ozone generated from a plasma device to inside duct and interior space.

6

Figure 8:
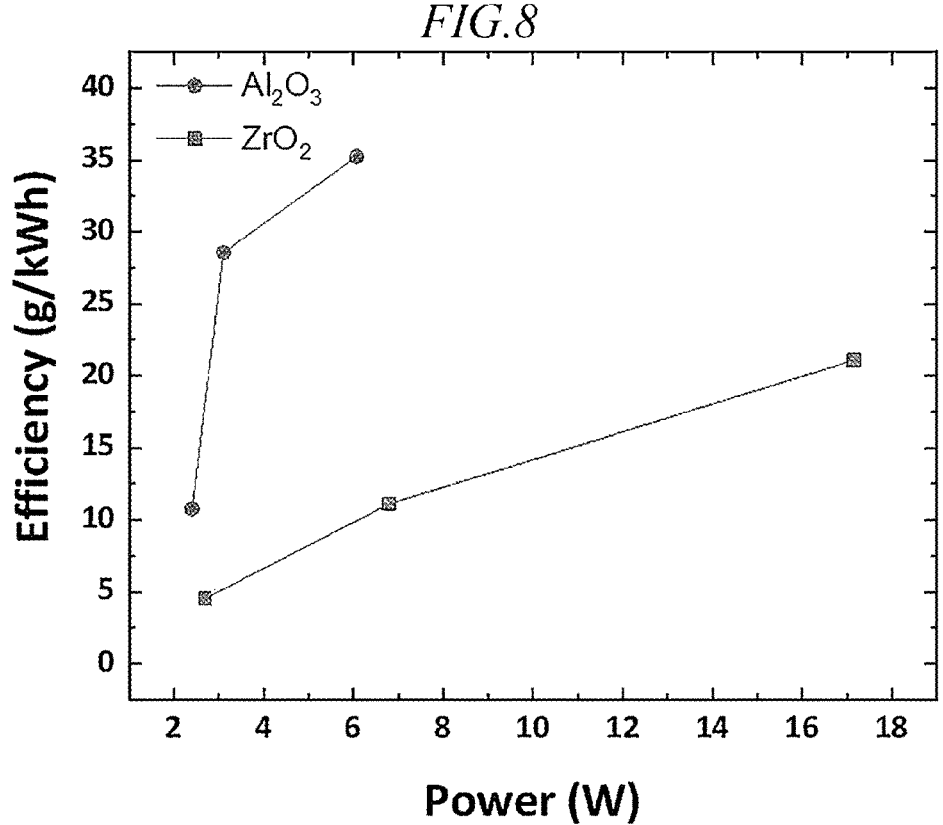

FIG. 8 is a graph illustrating results of measuring ozone generation efficiency of a plasma filter unit according to one embodiment.

Figure 9:
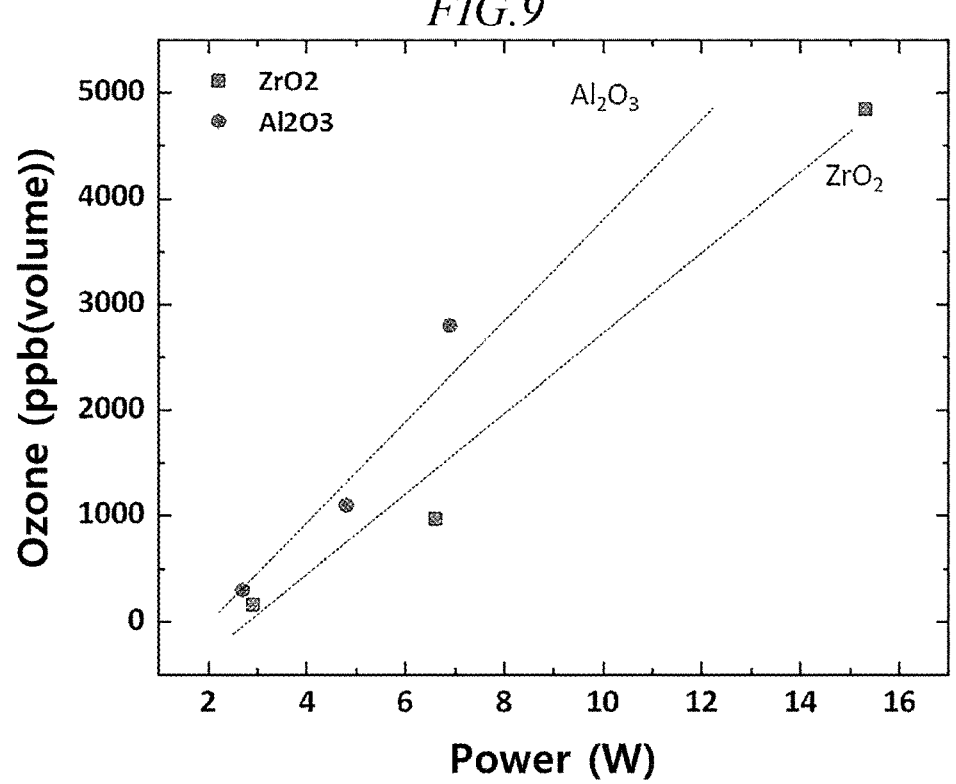

FIG. 9 is a graph illustrating results of measuring an ozone generation concentration of a plasma filter unit according to one embodiment.

FIG. 10 is an illustration of results of one embodiment with a catalyst unit which efficiently removes ozone generated from a plasma filter unit.

BEST MODE

The above object and means of this disclosure and the effects thereof will become more obvious from the following detailed description associated with the accompanying drawings. Therefore, those ordinarily skilled in the art to which this pertains may easily practice a technical idea of this disclosure. In addition, in describing this disclosure, when a detailed description of well-known technology relating to this disclosure may unnecessarily make unclear the spirit of this disclosure, a detailed description thereof will be omitted.

Terms used in the present specification are for explaining embodiments rather than limiting this disclosure. Unless otherwise stated, a singular form includes a plural form in the present specification. In this specification, terms such as "include," "comprise," "provide," or "have" do not exclude presence or addition of one or more other elements other than the mentioned elements.

In the present specification, terms such as "or," and "at least one," may indicate one of the words listed together, or a combination of two or more. For example, "A or B" or "at least one of A and B" may include only one of A or B, or both A and B.

In the present specification, descriptions according to "for example" and the like may not exactly match the presented information, such as recited properties, variables or values, and should not be construed as defining the embodiments of this disclosure according to various embodiments of this disclosure with effects such as variations, including tolerances, measurement errors, definitions of measurement accuracy and other factors commonly known.

As used herein, it is to be understood that when one component is referred to as being "connected to" or "coupled to" another component, one component may be connected directly to or coupled directly to another component or be connected to or coupled to another component with the other component interposed therebetween. On the other hand, it is to be understood that when one element is referred to as being "connected directly to" or "coupled directly to" another element, it may be connected to or coupled to another element without the other element intervening therebetween.

As used herein, when a component is described as being "on" or "contacting" another component, it may be directly in contact with or connected to other components, but it should be understood that another component may exist therebetween. On the other hand, when any component is described as being "directly on" or "directly contact with" other components, it may be understood that another element does not exist therebetween. Other expressions describing the relationship between the components, for example, "~between," "~directly between" and the like can be interpreted similarly.

As used herein, terms "first," "second" and the like, may be used to describe various components, but the components are not to be construed as being limited by these terms. In addition, the above term should not be construed as defining the order of each component, and may be used for the purpose of distinguishing one component from another. For example, a "first component" may be named a "second component" and the "second component" may also be similarly named the "first component."

Unless defined otherwise, all terms used in the present specification have the same meaning as meanings commonly understood by those skilled in the art to which this disclosure pertains. In addition, terms defined in commonly used dictionary are not ideally or excessively interpreted unless explicitly defined otherwise.

Hereinafter, preferred embodiments of this disclosure will be described in detail with reference to the accompanying drawings. However, embodiments below are merely preferred embodiments of this disclosure and this disclosure is not defined by embodiments below.

In addition, for the descriptions of the accompanying drawings, the same or corresponding components are given the same reference numerals without redundant descriptions on the reference numerals.

As used herein, the term "pathogen" refers to microorganisms that cause diseases, such as viruses and bacteria. In general, pathogens include anything that may cause disease.

As used herein, the term bio-aerosol includes airborne microorganisms, microorganisms such as bacteria or mold, viruses, pollen causing allergy, etc., which are contained in gas or liquid particles.

In the present specification, the description of sterilization or inactivation of bio-aerosols is used interchangeably with the meaning of removal of bio-aerosols.

[An Air Conditioning System for Disinfection of a Public Facility]

Figure 1:
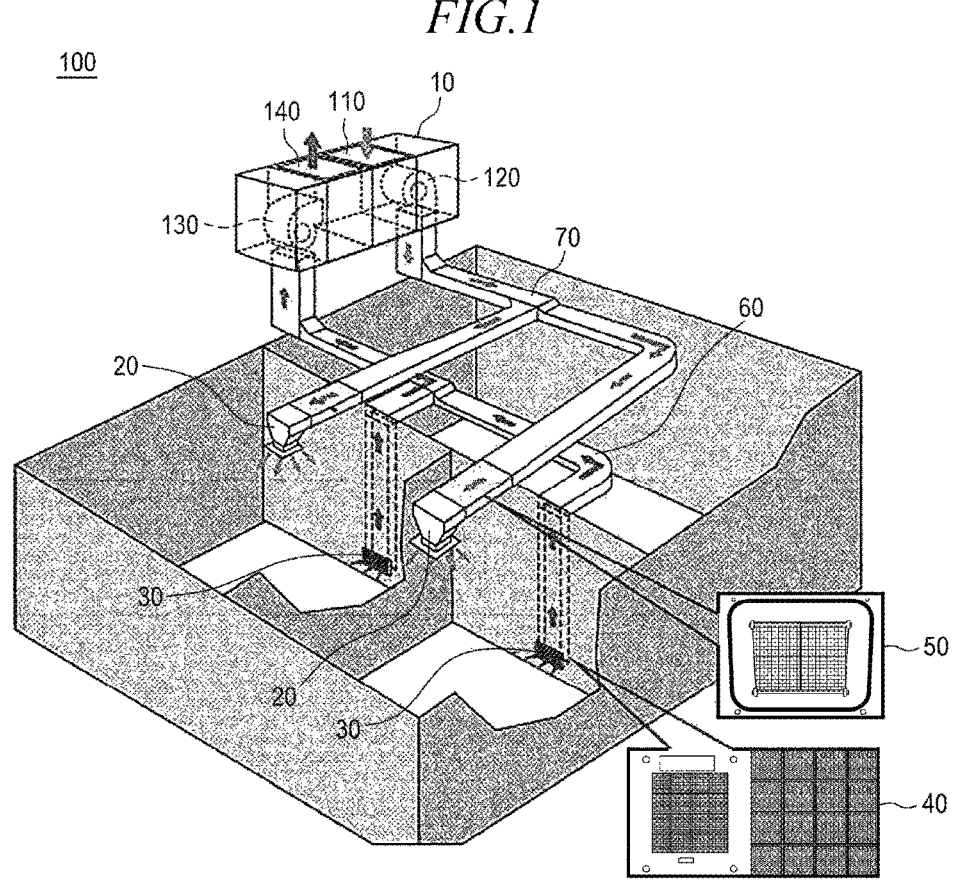
FIG. 1 is a schematic illustration of one embodiment of an air conditioning system for disinfection of a public facility.

FIG. 1 is a schematic illustration of one embodiment of an air conditioning system for disinfection of a public facility.

In FIG. 1, an air conditioning system 100 for disinfection of a public facility may comprise an air conditioning equipment 10 installed in a public facility structure; at least one air supply vent 20 through which air is introduced from the air conditioning equipment 10 to interior space of the public facility; at least one air inlet 30 through which air is exhausted from the interior space of the public facility to the air conditioning equipment 10; a plasma filter unit 40 installed in at least one of the air supply vent 20 and the air inlet 30 to collect contaminants in air and sterilize or inactivate them with plasma; and a catalyst unit 50 installed in at least one of the air supply vent 20 and the air inlet 30 to remove gaseous contaminants and ozone in air, wherein the air supply vent 20 and the air inlet 30 are installed in each of at least one separate room of the public facility and the plasma filter unit 40 installed in at least one of the air supply vent 20 and air inlet 30 is periodically or continuously operated to periodically or continuously sterilize or inactivate bio-aerosols collected in the plasma filter unit 40.

The air conditioning system for disinfection of a public facility may be easily applicable on hospitals, schools, public transportations, airports, etc. In addition, the air conditioning system for disinfection of a public facility easily applicable on collecting particulate materials and managing bio-aerosols and pathogens present in indoor air of the public facility may be provided.

The particulate contaminants include fine dusts and bio-aerosols.

The gaseous contaminants include volatile organic compounds.

This disclosure is not limited to, but in the present application, operation period of the plasma filter unit 40 in each of at least one separate room may be individually controlled. In the configuration, operation period of plasma filter unit 40 may be individually controlled according to characteristics and circumstances of a separate room. Accordingly, it is easy to suppress spread of bio-aerosols to other separate rooms and efficiently manage energy.

The plasma filter unit 40 may comprise, but not limited to, a plasma generator and a filter.

This disclosure is not limited to, the plasma generator comprises a porous ceramic dielectric and the porous ceramic dielectric may comprise an antibacterial coating layer coated with an antibacterial material. To generate plasma, corona discharge, arc discharge and dielectric barrier discharge, etc. may be applied. However, in this disclosure, dielectric barrier discharge may be the most advantageous for large-area discharge in the form of electric discharge.

The filter may be, but not limited to, at least one group of porous ceramic filters and polymer filters. The polymer filter may be at least one group of Pre filters, Medium filters and HEPA filters.

The porous ceramic may be, but not limited to, a bead or a reticulated porous ceramic. By adjusting the size of the bead in accordance to the features of spaces in the public facility, indoor air quality may be optimized. In addition, with pore density or porosity of the bead or the reticulated porous ceramic adjusted for properties of plasma, pressure loss of air conditioning system for disinfection may be minimized and air purification capacity may be increased.

Although not limited thereto, the plasma generator generates ozone when plasma is generated. Ozone is harmful to the human body due to its strong oxidizing characteristics, etc. When ozone remains in the atmosphere, there is a need to remove it. In this disclosure, ozone generated from the plasma may be removed in the catalyst unit 50. However, in one embodiment, disinfection method may be sterilization of pathogens and bio-aerosols by filling interior space with the generated ozone.

The catalyst unit 50 may comprise, but not limited to, at least one group of activated carbon and manganese oxide group. Use of activated carbon catalyst may bring about effective removal of ozone and deodorizing effects by absorbing ozone through gaps between activated carbons. In addition, use of manganese oxide group may bring about high efficiency in ozone removal as ozone is rapidly disintegrated by passing through the catalyst unit 50.

Furthermore, according to the configuration, coated layer of the porous ceramic dielectric with various sterilizing agents may provide an air conditioning system for disinfection of a public facility with plasma generator capable of effectively removing bio-aerosols, such as specific pathogens, etc.

Although not limited thereto, the catalyst unit 50 may remove bio-aerosols in the air which are not removed in the plasma filter unit 40 or remain within an air conditioning duct.

In the configuration of the air conditioning system for disinfection of a public facility, bio-aerosols and pathogens are effectively removed by plasma filter unit 40 and catalyst unit 50 to prevent spread of various bio-aerosols and pathogens in advance.

Figure 2:
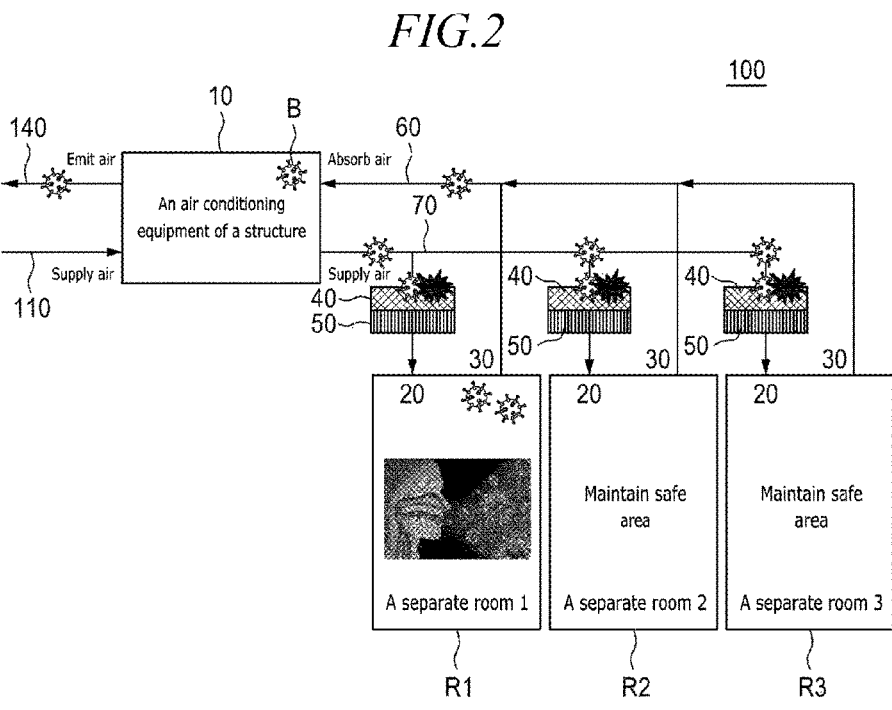
FIG. 2 is a schematic diagram of one embodiment of an air conditioning system for disinfection of a public facility with a plasma filter unit and a catalyst unit installed in an air supply vent.
Figure 3:
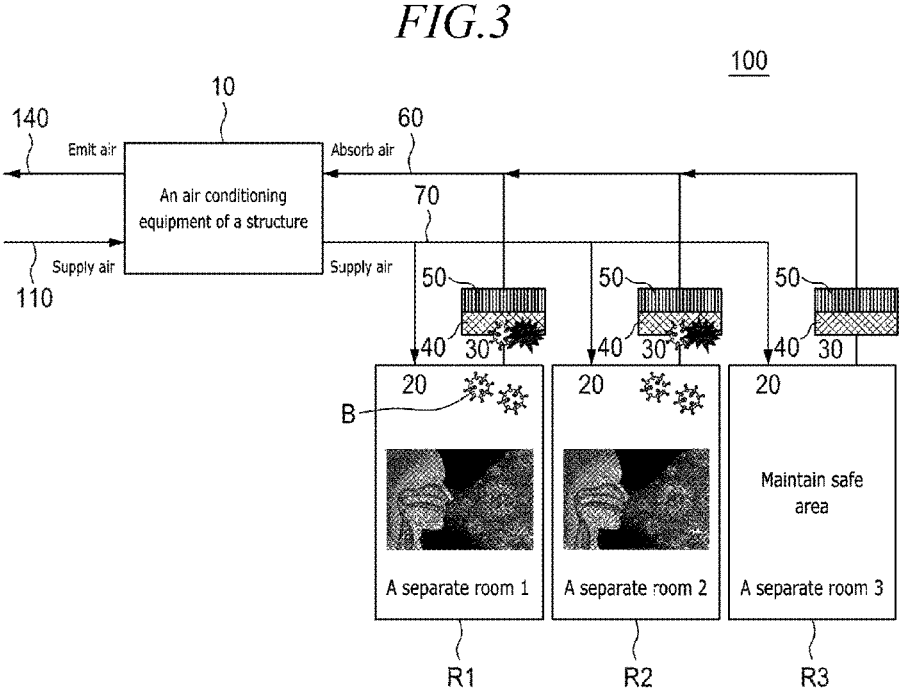
FIG. 3 is a schematic diagram of one embodiment of an air conditioning system for disinfection of a public facility with a plasma filter unit and a catalyst unit installed in an air inlet.

FIG. 2 is a schematic diagram of one embodiment of an air conditioning system for disinfection of a public facility with a plasma filter unit and a catalyst unit installed in an air supply vent. FIG. 3 is a schematic diagram of one embodiment of an air conditioning system for disinfection of a public facility with plasma filter unit and catalyst unit installed in air inlet.

In FIGS. 2 and 3, the plasma filter unit 40 and the catalyst unit 50 may be installed together in the air supply vent 20 or in the air inlet 30. In the configuration, ozone generated by plasma generated from the plasma filter unit 40 may be quickly removed.

In addition, the catalyst unit 50 is installed to remove ozone generated from the plasma filter unit 40 and prevent inflow of ozone into the air conditioning duct. As illustrated in FIG. 2, in case of the plasma filter unit 40 and the catalyst unit 50 installed together in the air supply vent 20, the plasma filter unit 40 is positioned far from the air supply vent 20 and the catalyst unit 50 is positioned close to the air supply vent 20 so that the remaining ozone is removed in catalyst unit 50 and prevented from flowing into the separate rooms R1-R3. As illustrated in FIG. 3, in case of the plasma filter unit 40 and the catalyst unit 50 installed together in the air inlet 30, the plasma filter unit 40 is positioned close to the air inlet 30 and the catalyst unit 50 is positioned far from the air inlet 30 so that the remaining ozone is removed in catalyst unit 50 and prevented from flowing into air conditioning duct.

Although not limited thereto, operation period of the plasma filter unit 40 in general disinfection mode is maintained at less than or equal to 50% of the entire operation period of the air conditioning system for disinfection. In the general disinfection mode, when contamination is not severe within a public facility, even if there is a person in the space, it is possible to periodically collect particulate matters in air and safely remove bio-aerosols.

Although not limited thereto, operation period of the plasma filter unit 40 in intensive disinfection mode is maintained at more than 50% to less than or equal to 100% of the entire operation period of the air conditioning system for disinfection. When contamination of interior space is severe, the operation in the intensive disinfection mode by continuously removing bio-aerosols in the air improves air quality of interior space more quickly and more effectively than the periodically operated general disinfection mode.

Although not limited thereto, wind speed under operation of the plasma filter unit 40 is less than or equal to 2 m/s. Concentration of ozone generated from the plasma filter unit 40 may be 0.5 to 100 ppm (volume). The wind speed improves efficiency of sterilization and/or inactivation of bio-aerosols in the air, which is the object of this disclosure, and may be controlled to remove ozone generated from the plasma filter unit 40. That is, high concentration of ozone may be generated during a part of the entire operation period to sterilize filter unit of the air conditioning air inlet and exhaust to outside. In addition, when the concentration of the ozone is less than 0.5 ppm (volume), the effect of sterilization and/or inactivation of bio-aerosols may be reduced.

Figure 4:
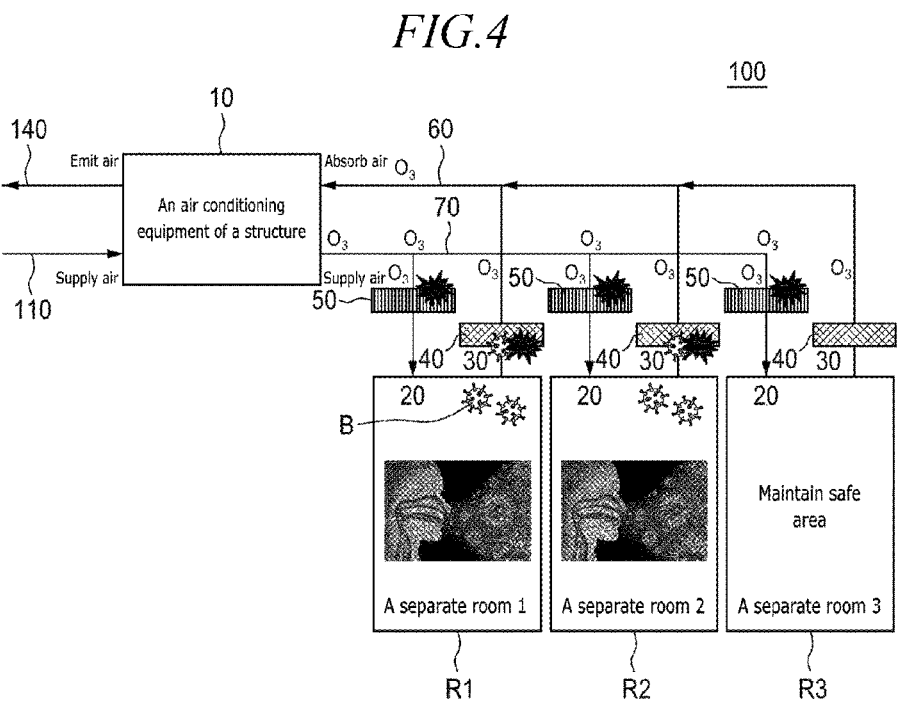
FIG. 4 is a schematic diagram of one embodiment of an air conditioning system for disinfection of a public facility with a plasma filter unit and a catalyst unit installed in separate positions.
Figure 5:
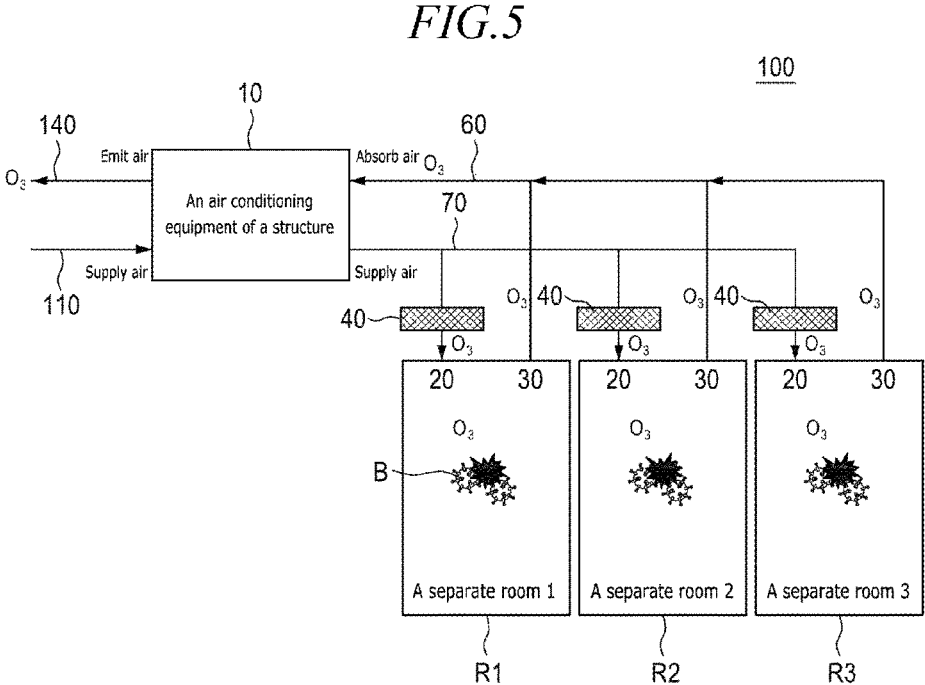
FIG. 5 is a schematic diagram of one embodiment of an air conditioning system capable of intensive disinfection of a public facility with a plasma filter unit in an air supply vent.

FIG. 4 is a schematic diagram of one embodiment of an air conditioning system for disinfection of a public facility with a plasma filter unit and a catalyst unit installed in separate positions. FIG. 5 is a schematic diagram of one embodiment of an air conditioning system capable of intensive disinfection of a public facility with a plasma filter unit in air supply vent.

In FIGS. 4 and 5, air conditioning system 100 of a public facility in another aspect may comprise: an air conditioning equipment 10 in a public facility structure 10; at least one air supply vent 20 through which air is introduced from the air conditioning equipment 10 to interior space of the public facility; at least one air inlet 30 through which air is exhausted from the interior space of the public facility to the air conditioning equipment 10; and a plasma filter unit 40 installed in at least one of the air supply vent 20 and air inlet 30 to collect particulate contaminants in the air and sterilize or inactivate with plasma; wherein the air supply vent 20 and the air inlet 30 are installed in each of at least one separate room of the public facility, and the plasma filter unit 40 installed in at least one of the air supply vent 20 and air inlet 30 is periodically or continuously operated to sterilize or inactivate bio-aerosols collected in the plasma filter unit 40.

In FIG. 4, the plasma filter unit 40 is installed in the air inlet 30 and the catalyst unit 50 removing gaseous contaminants and ozone in air is installed in the air supply vent 20 to prevent inflow of remaining ozone to interior space. In the configuration, as it effectively removes air contaminants in the air conditioning duct and the air conditioning equipment 10 twice with a time difference, it is more advantageous than the configuration of the plasma filter unit 40 and catalyst unit 50 installed together.

In the configuration, as the plasma filter unit 40 is installed in the air inlet 30, bio-aerosols and fine dusts may be removed primarily through the inlet duct (60 in FIG. 1) in prior to contamination of inside an air conditioning equipment 10 of a public facility by bio-aerosols and fine dusts generated from at least one separate room.

In addition, the primarily purified air as above may be subjected to the secondary purification to remove gaseous contaminants in the catalyst unit 50 installed in the air inlet 20 before flowing into at least one separate room and then supplied to at least one separate room through the air supply duct 70.

In FIG. 5, the plasma filter unit 40 is installed in the air supply vent 20. Operation time of the plasma filter unit 40 with at least one separate room emptied in intensive disinfection mode is maintained more than 50% to less than or equal to 100% of entire operation time. As generated ozone passes through the air inlet 30 and the air inlet duct 60, it is emitted to outside of the structure through the air conditioning equipment 10. In the configuration, during the intensive disinfection operation, ozone is supplied through air supply vent 20 of at least one separate room of a public facility with severe contamination. In completion of disinfection of a separate room, remaining ozone flowing through the air inlet 30 and the inlet duct 60 removes bio-aerosols and undesirable odors within the duct of the air conditioning equipment 10.

Under the intensive disinfection mode, the concentration of ozone within a separate room or air conditioning equipment 10 is maintained at, but not limited to, 0.5 to 100 ppm (volume). When the concentration of ozone is below 0.5 ppm (volume), effectiveness in sterilization and/or inactivation of bio-aerosols reduces and, when the concentration of ozone is above 100 ppm (volume), ozone may remain even after the disinfection is completed and ozone is emitted through the air inlet 30. It may affect the oxidation of the inner surface of the air conditioning duct.

Although not limited thereto, to optimally control the ozone concentration, a sensor for detecting the ozone concentration may be provided in at least one separate room or air conditioning equipment 10.

In another aspect, an air conditioning system 100 for disinfection of a public facility in this disclosure comprising; i) periodically sterilizing or inactivating bio-aerosols collected by the plasma filter unit 40 for a certain time by periodic operation of the plasma filter unit 40 installed in at least one of the air supply vent 20 and the air inlet 30 of at least one separate room; and ii) removing ozone generated from the plasma filter unit 40 in the catalyst unit 50, is provided.

Although it is not limited thereto, general disinfection mode of a public facility may comprise: in step i), collecting particulate matters and sterilizing or inactivating bio-aerosols with ozone in the plasma filter unit 40 by the plasma filter unit 40 and the catalyst unit 50 installed together in the air supply vent 20 or in the air inlet 30 of at least one separate room; and in step ii), removing ozone generated from the plasma filter unit 40 in the catalyst unit 50 before flowing into the interior space or the air conditioning duct; wherein operation period of the plasma filter unit 40 is maintained at less than or equal to 50% of the entire operation period of the air conditioning system.

In another aspect, as a method of disinfection using the air conditioning system for disinfection of a public facility of the present invention, an intensive disinfection method of a public facility comprising; i) sterilizing or inactivating bio-aerosols collected in the plasma filter unit 40 by continuous operation of the plasma filter unit 40 installed in at least one of the air supply vent 20 and the air inlet 30 of at least one separate room; and ii) operating in the intensive mode by maintaining operation period of the plasma filter unit 40 at more than 50% to less than or equal to 100% of the entire operation period and maintaining ozone concentration within the separate room or the air conditioning equipment 10 at 0.5 to 100 ppm (volume), is provided.

Although not limited thereto, the intensive disinfection method of a public facility may comprise: in step i), collecting particulate matters in the plasma filter unit 40 installed in the air inlet 30 of at least one separate room and sterilizing or inactivating bio-aerosols by ozone and removing ozone in the catalyst unit 50 installed in the air supply vent 20 of at least one separate room to prevent inflow of ozone to at least one separate room.

Although not limited thereto, the intensive disinfection method of a public facility ay comprise: step i), when at least one separate room is emptied, disinfecting at least one separate room by generating ozone from the plasma filter unit installed in the air supply vent 20 of at least one separate room; and, in completion of disinfection, emitting ozone remaining in the at least one separate room through the air inlet duct 60 connected to air inlet 30 of at least one separate room, passing the air conditioning equipment 10, and then to outside of the structure through internal gas outlet 140.

In the configuration, in case of severe contamination of indoor public facility, an air conditioning system for disinfection of a public facility capable of evacuation of humans and intensive disinfection including an operation mode to maintain high concentration of ozone by providing ozone generated from plasma generator to inside the duct and interior space may be provided.

Although not limited thereto, the intensive disinfection method of a public facility of a public facility may be operated in the periods, such as off-work hours, holidays, etc., when there are no humans in the indoor area of public facilities or when humans are evacuated from interior space contaminated with pathogens.

Hereinafter, a plasma filter unit 200 according to an embodiment of the present invention is specifically described.

Figure 6A:
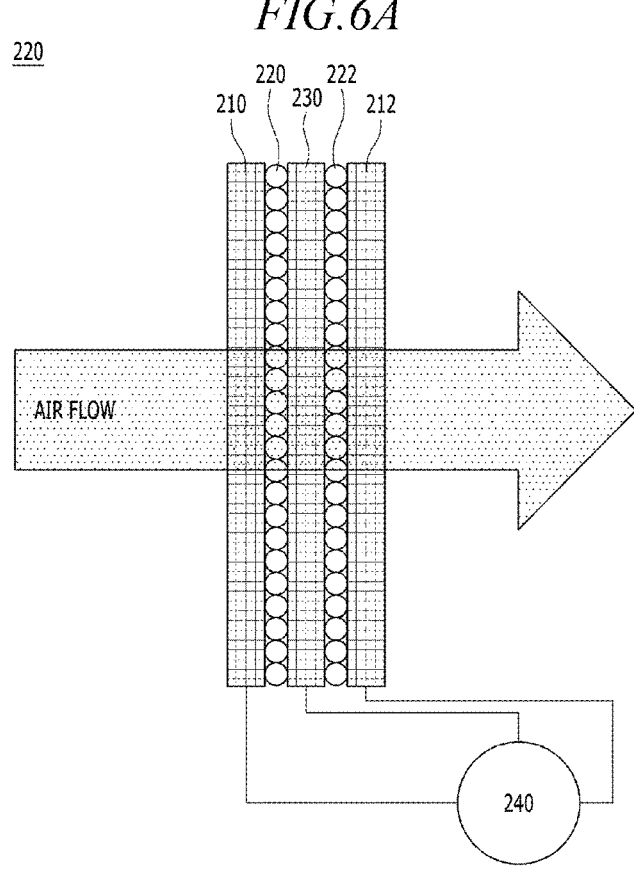
FIG. 6a is a schematic illustration of one embodiment of a plasma filter unit.

FIG. 6a is a schematic illustration of a plasma filter unit 200 in an embodiment of the present invention.

In FIG. 6a, plasma filter unit 200 of present invention comprises a first ground electrode 210; a high voltage electrode 230; and a first ceramic layer 220 made of a porous ceramic dielectric formed between the first ground electrode 210 and the high voltage electrode 230.

This disclosure is not limited thereto, but in the present application, dielectric barrier discharge may be most suitable to use large-area discharge in the form of electric discharge. The use of the dielectric barrier discharge has the advantage of obtaining a high concentration of active species per unit volume of the discharge area.

The first ground electrode 210 and the high voltage electrode 230 are made of a grid-like or porous metal such as a mesh. When power is applied to the high voltage electrode 230 by a high voltage power supply 240, a large amount of atmospheric pressure low-temperature plasma is generated at a portion in which the first ground electrode 210 and the high voltage electrode 230 are in contact with the dielectric ceramic. The metal is not limited thereto, but may include aluminum or stainless steel. With the above configuration, it is possible to effectively generate ozone for removing bacteria, viruses, etc., and it is possible to minimize pressure loss while increasing an air purification capacity.

A size and shape of the meshes of the first ground electrode 210 and the high voltage electrode 230 may be desirably adjusted to prevent the dielectric ceramic bead from leaking out.

The overall shape of the first ground electrode 210 and the high voltage electrode 230 may be a rectangular frame, but a shape of the frame may be changed according to a configuration of a conventionally applied air conditioner.

The ceramic comprises an antibacterial coating layer coated with an antibacterial material, and the ceramic layer is provided with open pores. With the above configuration, it is possible to effectively generate ozone for removing bacteria, viruses, etc., and it is possible to minimize pressure loss while increasing an air purification capacity.

The first ceramic layer is provided with the open pores, and thus, gas permeability is superior.

The plasma filter unit 200 may further comprise a second ceramic layer 222 made of a porous ceramic dielectric provided on one side of the high voltage electrode 230, and a second ground electrode 212 formed on one side of the second ceramic layer 222. The high voltage electrode 230, the second ceramic layer 222, and the second ground electrode 212 may increase a portion in contact with the porous ceramic dielectric to generate a large amount of atmospheric pressure low-temperature plasma. With the above configuration, it is possible to effectively generate ozone for removing bacteria, viruses, etc., and it is possible to minimize pressure loss while increasing an air purification capacity.

A porosity (ratio of space volume to total volume) of the first ground electrode 210, the high voltage electrode 230, and the second ground electrode 212 may be 5 to 95 vol %. Although not limited thereto, when the porosity of the first ground electrode 210, the high voltage electrode 230, and the second ground electrode 212 is less than 5 vol %, the pressure loss increases, and when the porosity of the first ground electrode 210, the high voltage electrode 230, and the second ground electrode 212 exceeds 95 vol %, plasma generation for collection and sterilization of the bio-aerosols may not be smoothly performed.

The thickness of the first ground electrode 210, the high voltage electrode 230, or the second ground electrode 212 may be 0.1 to 10 mm Although not limited thereto, when the thickness of the first ground electrode 210, the high voltage electrode 230, or the second ground electrode 212 is less than 0.1 mm, it is difficult to mechanically support the ceramic, and when the thickness of the first ground electrode 210, the high voltage electrode 230, or the second ground electrode 212 exceeds 10 mm, the first ground electrode 210, the high voltage electrode 230, or the second ground electrode 212 may take up more volume than necessary.

At least one of the first ceramic layer 220 and the second ceramic layer 222 may be formed as a single layer. With the above configuration, a large amount of atmospheric pressure low-temperature plasma may be generated by increasing a portion where the high voltage electrode 230 and the like is in contact with the porous ceramic dielectric. Accordingly, it is possible to efficiently remove pathogens, increase air purification capacity, and minimize pressure loss.

The ceramic layers 220 and 222 are for improving the removal efficiency of pathogens and contaminants by plasma, and the ceramics are not limited thereto, but may include at least one of alumina ($Al_2O_3$), zirconia ($ZrO_2$), diatomaceous earth, and silica ($SiO_2$).

An antibacterial coating layer of the ceramic may include at least one of zinc oxide having antibacterial activity and a carbon compound converting ozone into hydroxide. The zinc oxide and carbon compound may supply hydrogen peroxide or OH active species to the bio-aerosol collected in the ceramic layer to induce a sterilization effect and reduce ozone generated by plasma.

In addition, a ceramic filter coated with an antibacterial material that may implement antibacterial properties even under conditions in which plasma and ozone are not generated may have an antibacterial function.

The zinc oxide may include ZnOx, wherein x may be 1 to 2.

When the zinc oxide is coated on the surface of the porous ceramic, it may have a sterilization effect by a photocatalytic function by light, and may destroy cell walls of bacteria by ion substitution. In addition, it is possible to increase sterilization power against bacteria collected on the surface of the plasma module. In addition, the zinc oxide may have an antibacterial effect of sterilizing infectious bacteria attached to the air purifier for a long time.

The carbon compound converts ozone into an OH active species to lower the concentration of ozone and increase the sterilization activity. The carbon compound may exhibit a complex function by impregnating an antibacterial and dustproof material into granular activated carbon (AC). The granular activated carbon may form a surface layer of the high voltage electrode with fine particles in a colloidal form. Examples of the carbon compound may include zeolite or activated carbon.

The ceramic may be a bead or a reticulated porous ceramic.

The plasma filter unit of the present invention may comprise a first ceramic layer made of bead and a second ceramic layer made of bead; a first ceramic layer made of bead and a second ceramic layer made of reticulated porous ceramic; a first ceramic layer made of reticulated porous ceramic and a second ceramic layer made of bead; or a first ceramic layer made of reticulated porous ceramic and a second ceramic layer made of reticulated porous ceramic.

Figure 6B:
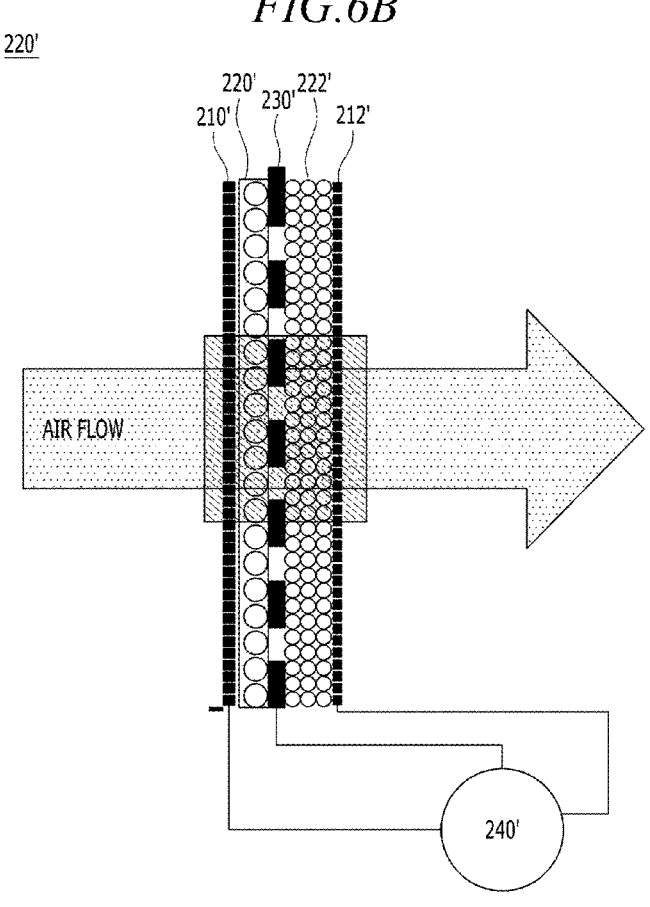
FIG. 6b is a schematic illustration of another embodiment of a plasma filter unit.

FIG. 6b is a schematic illustration of a plasma filter unit 200' in another embodiment of the present invention. FIG. 6b illustrates the plasma filter unit 200'; comprising a first ceramic layer 220' configured with bead and a second ceramic layer 222' configured with reticulated porous ceramic.

The ceramic layers 220', 222' in the present invention are formed as a single layer of porous ceramic and particle size of a bead in the ceramic layers 220', 222' may match a thickness of the ceramic layers 220', 222'. The particle size of the bead is correlated with the concentration of pathogens and the amount of ozone removed and, when the concentration of pathogens and ozone is high, the particle size of the bead may be decreased to increase a surface area. The bead in the ceramic layers 220', 222' typically has a larger diameter than an opening in the high voltage electrode 230' or the like. The ceramic layers 220', 222' may be fixed by an adhesive or a mechanical fastening structure and may be included before attachment to the high voltage electrode 230', etc., by assembly.

The particle size of the bead may be 100 to 5000 μm and it may be desirable, but not limited to, in increasing pathogen removal efficiency and ozone removal efficiency.

A porosity of at least one of the first ceramic layer 220' made of the bead and the second ceramic layer 222' made of the bead may be 0.5 to 50 vol %. Although not limited thereto, when the porosity of the first ceramic layer 220' and the second ceramic layer 222' is less than 0.5 vol %, the pressure loss increases and, when the porosity of the first ceramic layer 220' and the second ceramic layer 222' exceeds 50 vol %, the collection and sterilization of the bio-aerosols may be difficult or the air purification capacity may be reduced.

The pore distribution of the reticulated porous ceramic may be 30 to 100 pores per inch (PPI). Although not limited thereto, when the porosity distribution of the first ceramic layer 220' and the second ceramic layer 222' is less than 30 PPI, the pressure loss may increase and, when the porosity distribution of the first ceramic layer 220' and the second ceramic layer 222' exceeds 100 PPI, the collection and sterilization of the bio-aerosol may be difficult or the air purification capacity may be reduced.

The porosity of at least one of the first ceramic layer 220' made of the reticulated porous ceramic and the second ceramic layer 222' made of the bead may be 0.5 to 50 vol %.

The porosity of at least one of the first ceramic layer 220' made of the bead and the second ceramic layer 222' made of the reticulated porous ceramic may be 0.5 to 50 vol %.

Hereinafter, the present invention according to embodiments will be described more specifically.

EMBODIMENTS

Embodiment 1. An Air Conditioning System with a Plasma Filter Unit and a Catalyst Unit in Air Supply Vent for Disinfection of a Public Facility

[Air Conditioning System for Disinfection]

FIG. 2 is a schematic illustration of an embodiment of air conditioning system 100 with a plasma filter unit 40 and a catalyst unit 50 in an air supply vent 20 for disinfection of a public facility.

In FIG. 2, a plasma filter unit 40 and a catalyst unit 50 are installed together in an air supply vent 20 of an air conditioning equipment 20. At least one of the air supply vent 20 and air inlet 30 which are respectively connected to air supply duct 70 and air inlet duct 60 may be installed and connected to each separate room (R1 to R3).

[Disinfection Method]

1) General Disinfection Method

In FIGS. 1 and 2, air including bio-aerosol B in at least one separate room R1 of a public facility is absorbed through the air inlet 30, passes in the air inlet duct 60 through the air conditioning equipment 10 and exhausted by air fan 130 operation through internal gas outlet 140. In addition, external gas absorbed by the air fan 120 operation of the air conditioning equipment 10 through external gas inlet 110 passes through an air supply duct 70 to an air supply vent 20.

A porous ceramic or a polymer filter unit, as a filter unit of a plasma filter unit 40 installed in the air supply vent 20, collects bio-aerosols in the air.

Operation period of plasma filter unit 40 installed in the air supply vent 20 is maintained at less than or equal to 50% of the entire operation period. Based on the operation period, plasma is periodically generated from a plasma generator to sterilize and/or remove particulate contaminants and bio-aerosols collected in porous ceramic or polymer filter unit. Ozone and gaseous contaminants generated by plasma are removed by catalyst unit 50 before they flow into at least one separate room (R1 to R3). Then, the air with bio-aerosols and ozone removed is supplied to the separate room (R1 to R3).

2) Intensive Disinfection Method

In FIGS. 1 and 2, air including bio-aerosol B in at least one separate room R1 of a public facility is absorbed to an air inlet 30, pass in an air inlet duct 60 through an air conditioning equipment 10 and exhausted through an internal gas outlet 140 by an air fan 130 operation. In addition, external gas absorbed through external gas inlet 110 by the air fan 120 operation of the air conditioning equipment 10 passes through air supply duct 70 to air supply vent 20.

A porous ceramic or polymer filter, as a filter of a plasma filter unit 40 installed in the air supply vent 20, collects bio-aerosols in air.

Operation period of the plasma filter unit 40 installed in the air supply vent 20 is maintained at more than 50% to less than or equal to 100% of the entire operation period. Depending on the operation period, plasma is continuously generated from a plasma generator to sterilize and/or remove particulate contaminants and bio-aerosols collected in the porous ceramic or polymer filter unit. Ozone and gaseous contaminants generated by plasma are removed by a catalyst unit 50 before they enter at least one separate room (R1 to R3). Then, air with bio-aerosols and ozone removed is supplied to a separate room (R1 to R3).

In the configuration of an air conditioning system with the plasma filter unit 40 and the catalyst unit 50 installed together in the air supply vent 20 for disinfection, it is advantageous in preventing bio-aerosols generated from the separate room and bio-aerosols existing inside the air conditioning equipment 10 and the air conditioning duct from spreading to other separate rooms.

In addition, the air conditioning system for disinfection by the configuration of the plasma filter unit 40 and the catalyst unit 50 installed together in the air supply vent 20 may be easily applied to general public facilities, such as residential spaces, schools, public transportations, etc.

Embodiment 2. An Air Conditioning System for Disinfection of a Public Facility with a Plasma Filter Unit and a Catalyst Unit in an Air Inlet

[An Air Conditioning System for Disinfection]

FIG. 3 is a schematic diagram of one embodiment of an air conditioning system 100 for disinfection of a public facility with a plasma filter unit 40 and a catalyst unit 50 in an air inlet 30.

In FIG. 3, a plasma filter unit 40 and a catalyst unit 50 are installed together in an air inlet 30 installed in an air conditioning equipment 10. At least one air supply vent 20 and air inlet 30 respectively connected to an air supply duct 70 and an air inlet duct 60 may be respectively connected to a separate room (R1 to R3).

[Disinfection Method]

1) General Disinfection Method

In FIGS. 1 and 3, air including particulate matters and bio-aerosols B in at least one separate room R1 of a public facility is absorbed through an air inlet 30 and particulate matters and bio-aerosols in the air are collected in a porous ceramic or polymer filter, a filter of a plasma filter unit 40 installed in the air inlet 30.

Operation time of the plasma filter unit 40 installed in the air inlet 30 is maintained to be less than or equal to 50% of the entire operation period of the air conditioning system for disinfection. According to the operation period, plasma is periodically generated from a plasma generator and particulate contaminants and bio-aerosols collected in the porous ceramic or polymer filter unit are sterilized and/or removed. Ozone and gaseous contaminants generated by plasma are removed by the catalyst unit 50.

Air after removal of bio-aerosols and ozone flows in the air inlet duct 60 passing through the air conditioning equipment 10 and then are exhausted to internal gas outlet 140 by the operation of an air fan 130. In addition, external gas introduced through an external gas inlet 110 by operation of the air fan 120 of the air conditioning equipment 10 flows through an air supply duct 70 to be supplied from the air supply vent 20 to interior space.

2) Intensive Disinfection Method

In FIGS. 1 and 3, air including particulate matters and bio-aerosols B in at least one separate room R1, R2 of a public facility is absorbed through an air inlet 30 and particulate matters and bio-aerosols in the air are collected in a porous ceramic or polymer filter, a filter of a plasma filter unit 40 installed in the air inlet 30.

Operation time of the plasma filter unit 40 installed in the air inlet 30 is maintained at more than 50% to less than or equal to 100% of the entire operation period of the air conditioning system for disinfection. According to the operation period, plasma is continuously generated from a plasma generator and particulate contaminants and bio-aerosols collected in the porous ceramic or polymer filter unit are sterilized and/or removed. Ozone and gaseous contaminants generated by plasma are removed by the catalyst unit 50.

Air after removal of bio-aerosols and ozone flows in the air inlet duct 60 passing through the air conditioning equipment 10 and then are exhausted to internal gas outlet 140 by the operation of an air fan 130. In addition, external gas introduced through an external gas inlet 110 by operation of the air fan 120 of the air conditioning equipment 10 flows through an air supply duct 70 to be supplied from the air supply vent 20 to interior space.

According to the air conditioning system for disinfection by the configuration of the plasma filter unit 40 and the catalyst unit 50 installed in the air inlet 30, bio-aerosols B generated from at least one separate room R1, R2 are removed before contaminating inside the air conditioning equipment 10 and the air conditioning duct to prevent from contamination of other separate rooms.

In addition, the air conditioning system for disinfection by the configuration of the plasma filter unit 40 and the catalyst unit 50 installed in the air inlet 30 may be easily applied to air conditioning facilities such as wards of hospitals among public facilities.

Embodiment 3. An Air Conditioning System for
Disinfection of a Public Facility with a Filter Unit
and a Catalyst Unit Separated

[An Air Conditioning System for Disinfection]

FIG. 4 is a schematic diagram of one embodiment of an
air conditioning system for disinfection of a public facility
with a plasma filter unit and a catalyst unit installed in
separate positions.

In FIG. 4, an air conditioning equipment 10 is provided
with a plasma filter unit 40 in an air inlet 30 and a catalyst
unit 50 in an air supply vent 20 respectively. At least one of
the air supply vent 20 and air inlet 30 respectively connected
to the air supply duct 70 and air inlet duct 60 may be
installed to be respectively connected to a separate room R1
to R3.

[Disinfection Method]

1) General Disinfection Method

In FIGS. 1 and 4, air including bio-aerosols B in at least
one separate room R1, R2 of a public facility is absorbed
through an air inlet 30 and particulate matters and bio-
aerosols in the air are collected in a porous ceramic or
polymer filter, a filter of a plasma filter unit 40 installed in
the air inlet 30.

Operation time of the plasma filter unit 40 installed in the
air inlet 30 is maintained to be less than or equal to 50% of
the entire operation period of the air conditioning system for
disinfection. According to the operation period, plasma is
periodically generated from a plasma generator. Not only
particulate contaminants and bio-aerosols collected in a
porous ceramic filter or polymer filter but also bio-aerosols
inside the air conditioning equipment 10 are sterilized and/or
removed. At the same time, undesirable odor of the air
conditioning equipment 10 is also removed.

Ozone is generated by the generation of plasma. Air with
the generated ozone is absorbed by an air inlet 30, flows in
an air inlet duct 60 through the air conditioning equipment
10 and exhausted to an internal gas outlet 140 by operation
of an air fan 130. In addition, external gas introduced
through an external gas inlet 110 by operation of the air fan
120 of the air conditioning equipment 10 flows through an
air supply duct 70 towards a supply vent 20.

Ozone and gaseous contaminants in air are removed by a
catalyst unit 50 installed in the air supply vent 20. Remain-
ing bio-aerosols are also removed. The air after removal of
ozone and bio-aerosols is supplied to interior space through
the air supply vent 20.

2) Intensive Disinfection Method

In FIGS. 1 and 4, air including particulate matters and
bio-aerosols B in at least one separate room R1, R2 of a
public facility is absorbed through an air inlet 30 and
particulate matters and bio-aerosols in the air are collected
in a porous ceramic or polymer filter, a filter of a plasma
filter unit 40 installed in the air inlet 30.

Operation time of the plasma filter unit 40 installed in the
air inlet 30 is maintained to be more than 50% to less than
or equal to 100% of the entire operation period of the air
conditioning system for disinfection. According to the
operation period, plasma is continuously generated from a
plasma generator and not only particulate contaminants and
bio-aerosols collected in the porous ceramic or polymer
filter unit but also bio-aerosols inside the air conditioning
equipment 10 are sterilized and/or removed. At the same
time, undesirable odor of the air conditioning equipment 10
is also removed.

Ozone is generated by the generation of plasma. Air with
the generated ozone is absorbed by an air inlet 30, flows in an air inlet duct 60 through the air conditioning equipment
10 and exhausted to an internal gas outlet 140 by operation
of an air fan 130. In addition, external gas introduced
through an external gas inlet 110 by operation of the air fan
120 of the air conditioning equipment 10 flows through an
air supply duct 70 towards a supply vent 20.

Ozone and gaseous contaminants in air are removed by a
catalyst unit 50 installed in the air supply vent 20. Remain-
ing bio-aerosols are also removed. The air after removal of
ozone and bio-aerosols is supplied to interior space through
the air supply vent 20.

Only the plasma filter unit 40 may be installed in the air
inlet 30 to remove bio-aerosols in indoor air.

The air conditioning system for disinfection by the con-
figuration of the plasma filter unit 40 and the catalyst unit 50
installed separately may prevent the bio-aerosols generated
in a separate room from contaminating other separate rooms.
In addition, disinfection may be efficiently performed twice
with a time difference and undesirable odor of the air
conditioning equipment 10 is also removed.

The air conditioning system for disinfection by the con-
figuration of the plasma filter unit 40 and the catalyst unit 50
installed separately may be easily applied to the wards of
hospitals among public facilities.

Embodiment 4. An Air Conditioning System for
Disinfection of a Public Facility with a Plasma
Filter Unit Only

[An Air Conditioning System for Disinfection]

FIG. 5 is a schematic diagram of one embodiment of an
air conditioning system capable of intensive disinfection of
a public facility with a plasma filter unit 40 in air supply vent
20.

In FIG. 5, only a plasma filter unit 40 is installed in an air
supply vent 20 of an air conditioning equipment 10. At least
one air supply vent 20 is connected to an air supply duct 70
to be respectively connected to a separate room R1 to R3.

[Disinfection Method]

Intensive Disinfection Method

In FIGS. 1 and 5, operation time of the plasma filter unit
40 installed in the air supply vent 20 is maintained to be
more than 50% to less than or equal to 100% of the entire
operation period of the air conditioning system for disinfec-
tion. According to the operation period, plasma is continu-
ously generated from a plasma generator.

Ozone generated by continuous generation of plasma is
supplied to at least one contaminated separate room R1 to
R3 without humans inside. At this time, concentration of
ozone of interior space to which ozone is supplied may be
maintained at 0.5 to 100 ppm (volume).

The ozone supplied to interior space removes, sterilizes
and/or inactivates gaseous contaminants and bio-aerosols of
interior space, is absorbed through the air inlet 30, flows
inside an air inlet duct 60, passes through the air condition-
ing equipment 10 and is exhausted through an internal gas
outlet 140 by the operation of air fan 130. At the same time,
bio-aerosols inside the air conditioning equipment may be
sterilized and/or removed and undesirable odor of the air
conditioning equipment 10 is removed.

The air conditioning system for disinfection by the con-
figuration of an air supply vent 20 with the plasma filter unit
40 only may be easily applied to general public facilities,
such as residential spaces, schools, public transportations,
etc.

Specifically, the air conditioning system for disinfection
by the configuration of the air supply vent 20 with the plasma filter unit 40 only is suitable as a configuration of intensive and rapid disinfection in a closed state by emptying the interior space or a separate room when the interior space or a separate room of most public facilities is seriously contaminated with pathogens.

Figure 7:
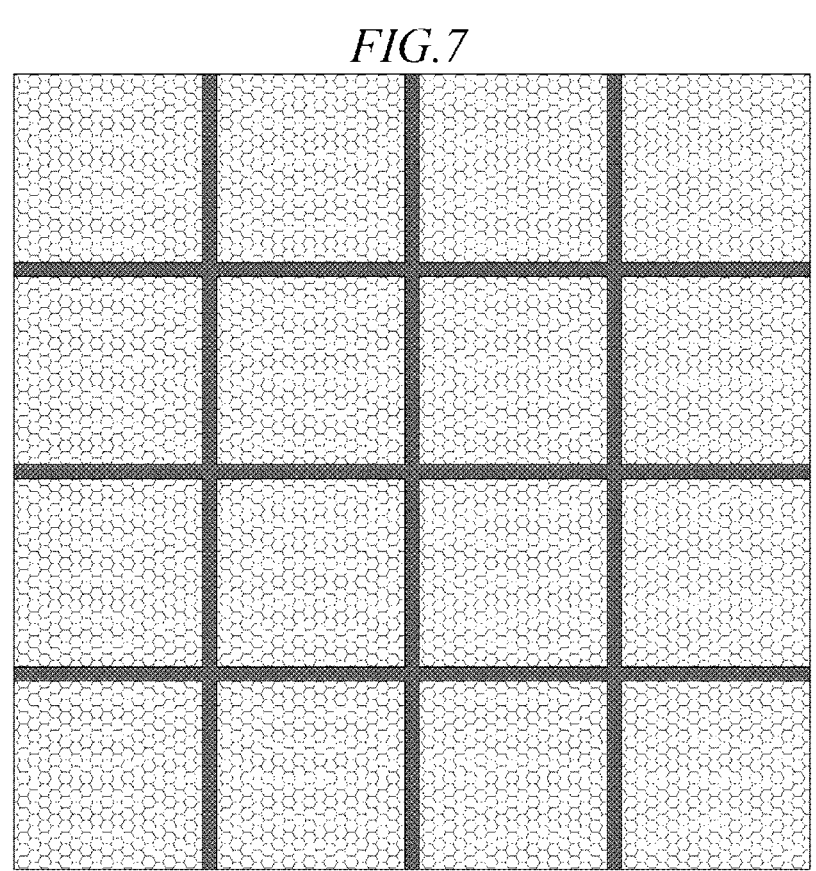
FIG. 7 is a photograph of one embodiment of a plasma filter unit.

Experimental Example 1. Measurement of Ozone Generation Efficiency and Ozone Generation Concentration of a Plasma Filter Unit A plasma filter unit (FIG. 7) of the present invention was prepared with an area of 100 mm in width and 100 mm in length. Ozone generation efficiency and ozone generation concentration according to ceramic material and power consumption were measured. An environment with a wind speed of 1 m/s was set on the duct of the area and the ozone concentration was measured in the rear of the plasma filter unit.

The results are illustrated in FIG. 8. FIG. 8 is a graph illustrating a results of measuring the ozone generation efficiency according to power consumption by the plasma filter unit of an embodiment.

A general ozone generation device is configured by a plasma generator unit for ozone generation with the length of tens of centimeters. Ozone generation efficiency of such ozone generator device is between 30 g/kWh and 40 g/kWh.

Meanwhile, as shown in FIG. 8, the plasma filter unit of the present invention in the condition of using alumina ceramic materials demonstrated ozone generation efficiency of at least 30 g/kWh, conventional level of ozone generator device, even with the length of plasma generator unit of less than or equal to 1 cm.

When the concentration of ozone for sterilization of bacteria in the air bio-aerosol is 0.5 ppm (volume) and the (volume) in power consumption of about 7 W. The zirconia materials were able to maintain wind speed of 1 m/s of air including ozone of about 5 ppm (volume) in power consumption of about 15 W. In the application of a plasma filter unit to an air conditioning, the ozone generation efficiency is sufficient to effectively sterilize and inactivate collected bio-aerosols.

Experimental Example 2. Evaluation of Ozone Generation and Emission Ozone Removal Characteristics of Air Purifier When the ozone removal catalyst unit is provided, it is possible to effectively reduce the concentration of ozone generated by the plasma filter unit. FIG. 10 is an illustration showing that gaseous ozone generated from a plasma filter unit of an embodiment is effectively removed by an ozone removal catalyst unit and that the concentration of emitted ozone is low. Ozone gas of 0.55 ppm (volume) was generated by applying power to the plasma generator in an environment in which air with a temperature of 22° C. and a humidity of 66% flows at a wind speed of 1 m/s in a cross-sectional area of 100 cm² of an air conditioning duct. As a result of applying gaseous ozone for 500 s through ozone removal catalyst based on carbon complex in the rear of a plasma generator unit in a condition of 22° C., the concentration of ozone emission was 72 ppb (volume)

Experimental Example 3. Evaluation of Antibacterial Properties of Plasma Filter After coating on the flexible dielectric using the ZnO-based antibacterial material of disclosure included in plasma filter, the antibacterial properties were evaluated. The results were shown in Tables 1 to 3.

TABLE 1

| | | Incubation time (Contact time) | | | | | |
| | | 2 h | | 4 h | | 24 h | |
| Specimen | | Reference (Untreated sample) | ZnO | Reference | ZnO | Reference | ZnO |
|---|---|---|---|---|---|---|---|
| *Staptyococcus aureus* (*S. aureus*) | Initial number of bacteria (Number of bacteria/cm²) | $2.2 \times 10^4$ | $1.4 \times 10^4$ | $2.2 \times 10^4$ | $1.4 \times 10^4$ | $1.4 \times 10^4$ | $1.4 \times 10^4$ |
| | After incubation (Number of bacteria/cm²) | $4.4 \times 10^2$ | <0.63 | $1.2 \times 10^3$ | <0.63 | $2.6 \times 10^4$ | <0.63 |
| | Bacterial reduction rate (%) | — | 99.9 | — | 99.9 | — | 99.9 |
| *Escherichia coli* (*E. coli*) | Initial number of bacteria (Number of bacteria/cm²) | $2.5 \times 10^4$ | $1.7 \times 10^4$ | $2.5 \times 10^4$ | $1.7 \times 10^4$ | $1.7 \times 10^4$ | $1.7 \times 10^4$ |
| | After incubation (Number of bacteria/cm²) | $1.5 \times 10^3$ | 3 | $1.3 \times 10^4$ | <0.63 | $1.1 \times 10^6$ | <0.63 |
| | Bacterial reduction rate (%) | — | 99.8 | — | 99.9 | — | 99.9 | exposure time is less than 10 minutes, it shows 99.9% sterilization properties of *Escherichia coli, Staphylococcus aureus, Legionella*, etc. The concentration of ozone of the air conditioning gas desired in this disclosure is 0.5 ppm (volume), and it is designed so that the bacteria in the bio-aerosol collected by the porous ceramic are exposed to ozone for several minutes or more. As it is designed to be exposed for more than a few minutes at a low concentration of ozone of 0.5 ppm (volume), the target concentration of ozone is low.

FIG. 9 is a result of measurement of ozone generation concentration according to power consumption and ceramic materials. The alumina materials were able to maintain wind speed of 1 m/s of air including ozone of about 3 ppm

TABLE 2

| | | Reference | ZnO |
|---|---|---|---|
| *Staphylococcus aureus* (*S.aureus*) | Initial number of bacteria (Number of bacteria/cm²) | $2.3 \times 10^6$ | $1.4 \times 10^4$ |
| | After 24 hours (Number of bacteria/cm²) | $2.8 \times 10^6$ | <0.63 |
| | Bacterial reduction rate (%) | — | 99.9 |
| *Klebsiella pneumonia* (*K.Pneumonia*) | Initial number of bacteria (Number of bacteria/cm²) | $2.7 \times 10^6$ | $1.7 \times 10^4$ |
| | After 24 hours (Number of bacteria/cm²) | $3.5 \times 10^7$ | <0.63 |
| | Bacterial reduction rate (%) | — | 99.9 |

21

TABLE 3

|  |  | Reference | ZnO |
|---|---|---|---|
| *Escherichia coli* (*E.coli*) | Initial number of bacteria (Number of bacteria/cm²) | $2.1 \times 10^5$ | $2.1 \times 10^5$ |
|  | After one hour (Number of bacteria/cm²) | $2.1 \times 10^5$ | <30 |
|  | Bacterial reduction rate (%) |  | 99.9 |

Table 1 showed the results of confirming the antibacterial ability of the ZnO-based antibacterial material, and was evaluated using the JIS ZX 2801 standard. It was confirmed that *Staphylococcus aureus* and *Escherichia coli* were reduced by more than 99.9% by the ZnO-based antibacterial material.

Table 2 showed the results of evaluating the antibacterial ability of the ZnO-based antibacterial material according to ASTM E 2180 standard which is a favorable condition for bacterial propagation compared to the conditions in Table 1. It was confirmed that *Staphylococcus aureus* and *Klebsiella pneumonia* were reduced by more than 99.9% after 24 hours by the ZnO-based antibacterial material.

Table 3 showed the results of evaluating the antibacterial ability of ZnO-based antibacterial materials according to ASTM E 2149 standard to confirm the antibacterial properties in a shorter time than the conditions in Table 2. It was confirmed that *Escherichia coli* was reduced by more than 99.9% after 1 hour by the ZnO-based antibacterial material.

Therefore, when the ZnO-based antibacterial material is coated inside the air purifier, it is possible to obtain the excellent antibacterial effect, and maximize the sterilization effect together with the ozone generated by the plasma generating module.

Although the specific embodiments according to this disclosure have been described so far, various modifications are possible without departing from the scope of this disclosure. Therefore, the scope of this disclosure is not limited to the described embodiments, and should be defined by the claims described below and their equivalents.

DESCRIPTION OF REFERENCE NUMERALS

10: air conditioning equipment
20: air supply vent
30: air inlet
40, 200, 200': plasma filter
50: catalyst unit
60: air inlet duct
70: air supply duct
100: air conditioning system for disinfection of a public facility
110: external gas inlet
120, 130: air fan
140: internal gas outlet
210, 210', 212, 212': ground electrode
220, 220', 222, 222': ceramic layer
230, 230': high voltage electrode
240, 240': high voltage power

The invention claimed is:

1. An air conditioning system for disinfection of a public facility, comprising:
an air conditioning equipment installed in a public facility structure;
at least one air supply vent through which air is introduced from the air conditioning equipment to interior space of the public facility;

22 at least one air inlet through which air is exhausted from the interior space of the public facility to the air conditioning equipment;
a plasma filter unit installed in at least one of the air supply vent and the air inlet to collect particulate contaminants in air and sterilize or inactivate bio-aerosols with plasma; and
a catalyst unit installed in at least one of the air supply vent and the air inlet to remove gaseous contaminants and ozone in air;
wherein the air supply vent and the air inlet are installed in each of at least one separate room of the public facility,
wherein the plasma filter unit comprises a plasma generator and a filter unit,
the plasma generator including a ground electrode, a high-voltage electrode, and a porous ceramic dielectric interposed between the ground electrode and the high-voltage electrode to generate atmospheric-pressure low-temperature plasma by dielectric barrier discharge, the porous ceramic dielectric comprising at least one of alumina ($Al_2O_3$), zirconia ($ZrO_2$), diatomaceous earth, and silica ($SiO_2$), wherein the plasma generator further comprising an antibacterial coating layer coated on the porous ceramic dielectric,
wherein the plasma filter unit and the catalyst unit are integrally installed together in at least one of the air supply vent and the air inlet of each separate room;
wherein, when the plasma filter unit and the catalyst unit are integrally installed together in the air supply vent, the catalyst unit and the plasma filter unit are sequentially arranged in order with respect to the air-supply direction such that particulate contaminants in the air are collected and bio-aerosols are sterilized or inactivated before the air flows into the separate room, and residual ozone and gaseous contaminants generated from the plasma generator are prevented from entering the indoor space of the separate room,
wherein, when the plasma filter unit and the catalyst unit are integrally installed together in the air inlet, the plasma filter unit and the catalyst unit are sequentially arranged in order with respect to the air-intake direction such that particulate contaminants in contaminated air of the separate room are collected and bio-aerosols are sterilized or inactivated by the plasma filter unit, thereby preventing particulate contaminants and bio-aerosols from entering an air-conditioning duct, and residual ozone and gaseous contaminants generated from the plasma generator are prevented from entering the air-conditioning duct, and
wherein the plasma filter unit installed in at least one of the air supply vent and air inlet is periodically or continuously operated to periodically or continuously sterilize or inactivate bio-aerosols collected in the plasma filter unit.

2. The air conditioning system for disinfection of a public facility of claim 1 capable of operation in a general disinfection mode, wherein operation period of the plasma filter unit is maintained at less than or equal to 50% of the entire operation period of the air conditioning system for disinfection.

3. The air conditioning system for disinfection of a public facility of claim 1 capable of operation in an intensive disinfection mode, wherein operation period of the plasma filter unit is maintained at more than 50% to less than or equal to 100% of the entire operation period of the air conditioning system for disinfection.

4. The air conditioning system for disinfection of a public facility of claim 1, wherein wind speed during operation of the plasma filter unit is less than or equal to 2 m/s and concentration of ozone generated from the plasma filter unit is 0.5 to 100 ppm (volume).

5. The air conditioning system for disinfection of a public facility of claim 1, > operation period of the plasma filter unit is individually controlled for each of at least one separate room.

6. The air conditioning system for disinfection of a public facility of claim 1, > the filter is at least one group of porous ceramic filters and polymer filters.

7. The air conditioning system for disinfection of a public facility of claim 6, > the porous ceramic is a bead or reticulated porous ceramic.

8. The air conditioning system for disinfection of a public facility of claim 1, > the catalyst unit comprises at least one group of activated carbons and manganese oxide groups.

9. The air conditioning system for disinfection of a public facility of claim 1, wherein the antibacterial coating layer comprises at least one of zinc oxide having antibacterial activity and a carbon compound converting ozone into hydroxide.

10. An air conditioning system for disinfection of a public facility, comprising:

> an air conditioning equipment installed in a public facility structure;
>
> at least one air supply vent through which air is introduced from the air conditioning equipment to interior space of the public facility;
>
> at least one air inlet through which air is exhausted from the interior space of the public facility to the air conditioning equipment; and
>
> a plasma filter unit installed in the air supply vent to collect particulate contaminants in gas and sterilize or inactivate bio-aerosols with plasma,
>
> wherein the air supply vent and the air inlet are installed in each of at least one separate room of the public facility,
>
> wherein the plasma filter unit comprises a plasma generator and a filter unit, the plasma generator including a ground electrode, a high-voltage electrode, and a porous ceramic dielectric interposed between the ground electrode and the high-voltage electrode to generate atmospheric-pressure low-temperature plasma by dielectric barrier discharge, wherein the porous ceramic dielectric comprising at least one of alumina ($Al_2O_3$), zirconia ($ZrO_2$), diatomaceous earth, and silica ($SiO_2$), wherein the plasma generator further comprising an antibacterial coating layer coated on the porous ceramic dielectric,
>
> wherein the plasma filter unit installed in the air supply vent is periodically or continuously operated to sterilize or inactivate bio-aerosols collected in the plasma filter unit,
>
> wherein, when at least one separate room is emptied, the system operates in an intensive disinfection mode in which an operation period of the plasma filter unit is maintained at 50% to 100% of an entire operation period of the air conditioning system for disinfection, and ozone generated from the plasma filter unit is discharged to the outside of the public facility through the air conditioning equipment via the air inlet.

11. The air conditioning system for disinfection of a public facility of claim 10, > wherein, during operation in the intensive disinfection mode, ozone concentration in the separate room or the air conditioning equipment is maintained at 0.5 to 100 ppm (volume).

12. The air conditioning system for disinfection of a public facility of claim 7, > operation period of the plasma filter unit is individually controlled for each of at least one separate room.

13. The air conditioning system for disinfection of a public facility of claim 10, further comprising a catalyst unit installed in the air supply vent and prevents flow of remaining ozone from flowing into interior space, > wherein the catalyst unit comprises at least one group of activated carbons and manganese oxide groups and is configured to remove gaseous contaminants and ozone in the air.

14. The air conditioning system for disinfection of a public facility of claim 10, wherein the antibacterial coating layer comprises at least one of zinc oxide having antibacterial activity and a carbon compound converting ozone into hydroxide.

15. A method of general disinfection of a public facility using the air conditioning system for disinfection of a public facility of claim 1, comprising:

> i) periodically sterilizing or inactivating bio-aerosols collected in the plasma filter unit for certain period by periodic operation of the plasma filter unit installed in at least one of the air supply vent and the air inlet of at least one separate room; and
>
> ii) removing ozone generated from the plasma filter unit in the catalyst unit.

16. The general disinfection method of a public facility of claim 15, comprising:

> in step i), collecting particulate matters and sterilizing or inactivating bio-aerosols with ozone in the plasma filter unit by the plasma filter unit and the catalyst unit installed together in the air supply vent or in the air inlet of at least one separate room; and,
>
> in step ii), removing ozone generated from the plasma filter unit in the catalyst unit before flowing into the interior space or the air conditioning duct,
>
> wherein operation period of the plasma filter unit is maintained at less than or equal to 50% of the entire operation period of the air conditioning system.

17. An intensive disinfection method of a public facility using the air conditioning system for disinfection of a public facility of claim 1, comprising:

> i) continuously sterilizing or inactivating bio-aerosols collected in the plasma filter unit by continuous operation of the plasma filter unit installed in at least one of the air supply vent and air inlet of at least one separate room; and
>
> ii) operating in an intensive disinfection mode by maintaining operation period of the plasma filter unit at more than 50% to less than or equal to 100% of the entire operation period and maintaining ozone concentration in the separate room or the air conditioning equipment at 0.5 to 100 ppm (volume).

18. The intensive disinfection method of a public facility of claim 17, comprising:

> in step i),
>
> > collecting particulate matters in the plasma filter unit installed in the air inlet of at least one separate room and sterilizing or inactivating bio-aerosols by ozone and removing ozone in the catalyst unit installed in the air supply vent of at least one separate room to prevent inflow of ozone to at least one separate room.

19. The intensive disinfection method of a public facility of claim 17, comprising:

in step i), when at least one separate room is emptied, disinfecting at least one separate room by generating ozone from the plasma filter unit installed in the air supply vent of at least one separate room; and, in completion of the disinfection, emitting remaining ozone in at least one separate room through the air inlet of at least one separate room by passing the air conditioning equipment to outside of the structure.

* * * * *